United States Patent
Lang et al.

(10) Patent No.: US 8,000,441 B2
(45) Date of Patent: *Aug. 16, 2011

(54) CALIBRATION DEVICES AND METHODS OF USE THEREOF

(75) Inventors: Philipp Lang, Lexington, MA (US); Siau-Way Liew, Pinole, CA (US)

(73) Assignee: ImaTx, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/505,908

(22) Filed: Jul. 20, 2009

(65) Prior Publication Data

US 2010/0014636 A1    Jan. 21, 2010

Related U.S. Application Data

(63) Continuation of application No. 12/055,491, filed on Mar. 26, 2008, now Pat. No. 7,580,504, which is a continuation of application No. 10/917,848, filed on Aug. 12, 2004, now Pat. No. 7,467,892, which is a continuation-in-part of application No. 10/225,363, filed on Aug. 20, 2002, now Pat. No. 7,050,534, which is a continuation-in-part of application No. 10/086,653, filed on Feb. 27, 2002, now Pat. No. 6,904,123, which is a continuation-in-part of application No. 09/942,528, filed on Aug. 29, 2001, now Pat. No. 7,545,964.

(60) Provisional application No. 60/228,591, filed on Aug. 29, 2000.

(51) Int. Cl.
*G01N 23/06* (2006.01)

(52) U.S. Cl. .............................. 378/56; 378/62; 378/207
(58) Field of Classification Search ................... 378/53, 378/54, 56, 62, 207; 382/130, 131, 132
See application file for complete search history.

(56) References Cited

U.S. PATENT DOCUMENTS

| | | | | |
|---|---|---|---|---|
| 2,274,808 | A | 3/1942 | Rinn | 250/69 |
| 3,924,133 | A | 12/1975 | Reiss | 250/408 |
| 4,012,638 | A | 3/1977 | Altschuler et al. | 250/491 |
| 4,126,789 | A | 11/1978 | Vogl et al. | 250/505 |
| 4,233,507 | A | 11/1980 | Volz | 250/252 |
| 4,251,732 | A | 2/1981 | Fried | 250/479 |
| 4,298,800 | A | 11/1981 | Goldman | 250/445 T |
| 4,356,400 | A | 10/1982 | Polizzi et al. | 378/138 |
| 4,400,827 | A | 8/1983 | Spears | 378/207 |
| 4,593,400 | A | 6/1986 | Mouyen | 378/99 |
| 4,649,561 | A | 3/1987 | Arnold | 378/207 |
| 4,686,695 | A | 8/1987 | Macovski | 378/146 |

(Continued)

FOREIGN PATENT DOCUMENTS

CA    2342344    3/2000

(Continued)

OTHER PUBLICATIONS

Baker, "Case Method: Entity Relationship Modeling" (Computer Aided Systems Engineering), 1$^{st}$ Ed., Addison-Wesley Longman Pub. Co., Inc., publisher, 2 pages. (Abstract Pages Only) (1990).

(Continued)

*Primary Examiner* — Courtney Thomas
(74) *Attorney, Agent, or Firm* — Sunstein Kann Murphy & Timbers LLP

(57) ABSTRACT

The present invention relates to calibration devices and to methods of using these devices.

18 Claims, 5 Drawing Sheets

U.S. PATENT DOCUMENTS

| | | | | |
|---|---|---|---|---|
| 4,721,112 A | 1/1988 | Hirano et al. | | 128/659 |
| 4,782,502 A | 11/1988 | Schultz | | 378/18 |
| 4,922,915 A | 5/1990 | Arnold et al. | | 128/653 R |
| 4,956,859 A | 9/1990 | Lanza et al. | | 378/157 |
| 4,985,906 A | 1/1991 | Arnold | | 378/18 |
| 5,001,738 A | 3/1991 | Brooks | | 378/170 |
| 5,090,040 A | 2/1992 | Lanza et al. | | 378/62 |
| 5,122,664 A | 6/1992 | Ito et al. | | 250/327.2 |
| 5,127,032 A | 6/1992 | Lam et al. | | 378/189 |
| 5,150,394 A | 9/1992 | Karellas | | 378/62 |
| 5,172,695 A | 12/1992 | Cann et al. | | 128/653.1 |
| 5,187,731 A | 2/1993 | Shimura | | 378/207 |
| 5,200,993 A | 4/1993 | Wheeler et al. | | 379/96 |
| 5,222,021 A | 6/1993 | Feldman et al. | | 364/413.14 |
| 5,228,445 A | 7/1993 | Pak et al. | | 128/660.01 |
| 5,235,628 A | 8/1993 | Kalender | | 378/207 |
| 5,247,934 A | 9/1993 | Wehrli et al. | | 128/653.2 |
| 5,270,651 A | 12/1993 | Wehrli | | 324/308 |
| 5,271,401 A | 12/1993 | Fishman | | 128/654 |
| 5,320,102 A | 6/1994 | Paul et al. | | 128/653.2 |
| 5,335,260 A | 8/1994 | Arnold | | 378/207 |
| 5,384,643 A | 1/1995 | Inga et al. | | 358/403 |
| 5,476,865 A | 12/1995 | Panetta et al. | | 514/369 |
| 5,493,593 A | 2/1996 | Müller et al. | | 378/19 |
| 5,493,601 A | 2/1996 | Fivez et al. | | 378/207 |
| 5,513,240 A | 4/1996 | Hausmann et al. | | 378/170 |
| 5,521,955 A | 5/1996 | Gohno et al. | | 378/18 |
| 5,537,483 A | 7/1996 | Stapleton et al. | | 382/309 |
| 5,562,448 A | 10/1996 | Mushabac | | 433/215 |
| 5,565,678 A | 10/1996 | Manian | | 250/252.1 |
| 5,592,943 A | 1/1997 | Buhler et al. | | 128/661.03 |
| 5,600,574 A | 2/1997 | Reitan | | 364/552 |
| 5,657,369 A | 8/1997 | Stein et al. | | 378/208 |
| 5,673,298 A | 9/1997 | Mazess | | 378/54 |
| 5,687,210 A | 11/1997 | Maitrejean et al. | | 378/57 |
| 5,769,072 A | 6/1998 | Olsson et al. | | 128/205.13 |
| 5,769,074 A | 6/1998 | Barnhill et al. | | 128/630 |
| 5,772,592 A | 6/1998 | Cheng et al. | | 600/407 |
| 5,852,647 A | 12/1998 | Schick et al. | | 378/53 |
| 5,864,146 A | 1/1999 | Karellas | | 250/581 |
| 5,886,353 A | 3/1999 | Spivey et al. | | 250/370.09 |
| 5,915,036 A | 6/1999 | Grunkin et al. | | 382/132 |
| 5,917,877 A | 6/1999 | Chiabrera et al. | | 378/5.3 |
| 5,931,780 A | 8/1999 | Giger et al. | | 600/407 |
| 5,945,412 A | 8/1999 | Fuh et al. | | 514/176 |
| 5,948,692 A | 9/1999 | Miyauti et al. | | 436/501 |
| 6,029,078 A | 2/2000 | Weinstein et al. | | 600/407 |
| 6,064,716 A | 5/2000 | Siffert et al. | | 378/53 |
| 6,077,224 A | 6/2000 | Lang et al. | | 600/407 |
| 6,108,635 A | 8/2000 | Herren et al. | | 705/2 |
| 6,156,799 A | 12/2000 | Hartke et al. | | 514/573 |
| 6,178,225 B1 | 1/2001 | Zur et al. | | 378/98.2 |
| 6,205,348 B1 | 3/2001 | Giger et al. | | 600/407 |
| 6,215,846 B1 | 4/2001 | Mazess et al. | | 378/54 |
| 6,226,393 B1 | 5/2001 | Grunkin et al. | | 382/128 |
| 6,246,745 B1 | 6/2001 | Bi et al. | | 378/54 |
| 6,248,063 B1 | 6/2001 | Barnhill et al. | | 600/300 |
| 6,249,692 B1 | 6/2001 | Cowin | | 600/407 |
| 6,252,928 B1 | 6/2001 | MacKenzie | | 378/54 |
| 6,285,901 B1 | 9/2001 | Taicher et al. | | 600/410 |
| 6,289,115 B1 | 9/2001 | Takeo | | 382/130 |
| 6,302,582 B1 | 10/2001 | Nord et al. | | 378/207 |
| 6,306,822 B1 | 10/2001 | Kumagai et al. | | 514/7 |
| 6,315,553 B1 | 11/2001 | Sachdeva et al. | | 433/24 |
| 6,320,931 B1 | 11/2001 | Arnold | | 378/56 |
| 6,377,653 B1 | 4/2002 | Lee et al. | | 378/54 |
| 6,411,729 B1 | 6/2002 | Grunkin | | 382/132 |
| 6,430,427 B1 | 8/2002 | Lee et al. | | 600/407 |
| 6,442,287 B1 | 8/2002 | Jiang et al. | | 382/128 |
| 6,449,502 B1 | 9/2002 | Ohkubo | | 600/407 |
| 6,463,344 B1 | 10/2002 | Pavloskaia et al. | | 700/98 |
| 6,501,827 B1 | 12/2002 | Takasawa | | 378/116 |
| 6,556,698 B1 | 4/2003 | Diano et al. | | 382/132 |
| 6,690,761 B2 | 2/2004 | Lang et al. | | 378/56 |
| 6,694,047 B1 | 2/2004 | Farrokhnia et al. | | 382/132 |
| 6,717,174 B2 | 4/2004 | Karellas | | 250/582 |
| 6,799,066 B2 | 9/2004 | Steines et al. | | 600/407 |
| 6,807,249 B2 | 10/2004 | Dinten et al. | | 378/54 |
| 6,811,310 B2 | 11/2004 | Lang et al. | | 378/169 |
| 6,824,309 B2 | 11/2004 | Robert-Coutant et al. | | 378/207 |
| 6,829,378 B2 | 12/2004 | DiFilippo et al. | | 382/128 |
| 6,835,377 B2 | 12/2004 | Goldberg et al. | | 424/93.7 |
| 6,836,557 B2 | 12/2004 | Tamez-Pena et al. | | 382/128 |
| 6,895,077 B2 | 5/2005 | Karellas et al. | | 378/98.3 |
| 6,904,123 B2 | 6/2005 | Lang | | 378/54 |
| 6,934,590 B2 | 8/2005 | Ogawa | | 700/19 |
| 6,975,894 B2 | 12/2005 | Wehrli et al. | | 600/407 |
| 7,050,534 B2 | 5/2006 | Lang | | 378/54 |
| 7,058,159 B2 | 6/2006 | Lang et al. | | 378/54 |
| 7,120,225 B2 | 10/2006 | Lang et al. | | 378/54 |
| 7,184,814 B2 | 2/2007 | Lang et al. | | 600/416 |
| 7,239,908 B1 | 7/2007 | Alexander et al. | | 600/427 |
| 7,245,697 B2 | 7/2007 | Lang | | 378/54 |
| 7,283,857 B1 | 10/2007 | Fallon et al. | | 600/407 |
| 7,292,674 B2 | 11/2007 | Lang | | 378/54 |
| 7,379,529 B2 | 5/2008 | Lang | | 378/54 |
| 7,467,892 B2 | 12/2008 | Lang et al. | | 378/207 |
| 7,545,964 B2 | 6/2009 | Lang et al. | | 382/128 |
| 7,580,504 B2 * | 8/2009 | Lang et al. | | 378/56 |
| 7,660,453 B2 | 2/2010 | Lang | | 382/132 |
| 7,664,298 B2 | 2/2010 | Lang et al. | | 382/128 |
| 7,676,023 B2 | 3/2010 | Lang | | 378/54 |
| 7,840,247 B2 | 11/2010 | Liew et al. | | 600/407 |
| 2002/0087274 A1 | 7/2002 | Alexander et al. | | 702/19 |
| 2002/0159567 A1 | 10/2002 | Sako et al. | | 378/117 |
| 2002/0186818 A1 | 12/2002 | Arnaud et al. | | 378/165 |
| 2002/0194019 A1 | 12/2002 | Evertsz | | 705/2 |
| 2002/0196966 A1 | 12/2002 | Jiang et al. | | 382/132 |
| 2003/0015208 A1 | 1/2003 | Lang et al. | | 128/922 |
| 2003/0198316 A1 | 10/2003 | Dewaele et al. | | 378/54 |
| 2004/0106868 A1 | 6/2004 | Liew et al. | | 600/442 |
| 2004/0247074 A1 | 12/2004 | Langton | | 378/54 |
| 2005/0015002 A1 | 1/2005 | Dixon et al. | | 600/407 |
| 2005/0148860 A1 | 7/2005 | Liew et al. | | 600/410 |
| 2005/0240096 A1 | 10/2005 | Ackerman et al. | | 600/410 |
| 2006/0062442 A1 | 3/2006 | Arnaud et al. | | 382/128 |
| 2007/0047794 A1 | 3/2007 | Lang et al. | | 382/132 |
| 2007/0274442 A1 | 11/2007 | Gregory et al. | | 378/54 |
| 2008/0031412 A1 | 2/2008 | Lang et al. | | 378/54 |
| 2008/0058613 A1 | 3/2008 | Lang et al. | | 600/300 |
| 2008/0097794 A1 | 4/2008 | Arnaud et al. | | 705/3 |
| 2008/0219412 A1 | 9/2008 | Lang | | 378/207 |
| 2009/0207970 A1 | 8/2009 | Lang | | 378/38 |
| 2009/0225958 A1 | 9/2009 | Lang | | 378/207 |
| 2010/0014636 A1 | 1/2010 | Lang et al. | | 378/56 |
| 2010/0098212 A1 | 4/2010 | Lang | | 378/54 |
| 2010/0130832 A1 | 5/2010 | Lang et al. | | 600/300 |
| 2010/0197639 A1 | 8/2010 | Lang et al. | | 514/143 |

FOREIGN PATENT DOCUMENTS

| | | |
|---|---|---|
| DE | 19853965 | 5/2000 |
| EP | 0314506 | 5/1989 |
| EP | 0797952 | 10/1997 |
| EP | 0570936 | 8/2000 |
| EP | 0678191 | 2/2001 |
| EP | 1230896 | 8/2002 |
| EP | 1283492 | 2/2003 |
| EP | 1349098 | 10/2003 |
| EP | 1357480 | 10/2003 |
| EP | 1424650 | 6/2004 |
| EP | 1598778 | 11/2005 |
| EP | 1069395 | 7/2006 |
| GB | 2023920 | 1/1980 |
| JP | 62 266053 | 11/1987 |
| JP | 05 099829 | 4/1993 |
| JP | 08 186762 | 7/1996 |
| JP | 10 145396 | 5/1998 |
| JP | 10 262959 | 10/1998 |
| JP | 11 069136 | 3/1999 |
| JP | 11 112877 | 4/1999 |
| JP | 2002 045722 | 2/2000 |
| JP | 2000 126168 | 5/2000 |
| JP | 2000 139889 | 5/2000 |
| JP | 2003 230557 | 8/2003 |
| WO | WO 94/012855 | 6/1994 |
| WO | WO 95/014431 | 6/1995 |
| WO | WO 99/008597 | 2/1999 |

| | | |
|---|---|---|
| WO | WO 99/045371 | 9/1999 |
| WO | WO 99/052331 | 10/1999 |
| WO | WO 00/033157 | 6/2000 |
| WO | WO 00/072216 | 11/2000 |
| WO | WO 01/038824 | 5/2001 |
| WO | WO 01/063488 | 8/2001 |
| WO | WO 01/065449 | 9/2001 |
| WO | WO 02/017789 | 3/2002 |
| WO | WO 02/022014 | 3/2002 |
| WO | WO 02/030283 | 4/2002 |
| WO | WO 02/096284 | 12/2002 |
| WO | WO 03/071934 | 9/2003 |
| WO | WO 03/073232 | 9/2003 |
| WO | WO 03/088085 | 10/2003 |
| WO | WO 2004/019256 | 3/2004 |
| WO | WO 2004/025541 | 3/2004 |
| WO | WO 2004/062495 | 7/2004 |
| WO | WO 2004/086972 | 10/2004 |
| WO | WO 2004/096048 | 11/2004 |
| WO | WO 2005/027732 | 3/2005 |
| WO | WO 2006/033712 | 3/2006 |
| WO | WO 2006/034018 | 3/2006 |
| WO | WO 2008/034101 | 3/2008 |
| WO | WO 99/045845 | 9/2009 |

OTHER PUBLICATIONS

Bauer et al., "Biochemical Markers of Bone Turnover and Prediction of Hip Bone Loss in Older Women: The Study of Osteoporotic Fractures," *Journal of Bone and Mineral Research*, vol. 14, pp. 1404-1410 (1999).

Beck et al., "Experimental Testing of a DEXA-Derived Curved Beam Model of the Proximal Femur," Journal of Orthopaedic Research, vol. 16, No. 3, pp. 394-398 (1998).

Black et al., "An Assessment Tool for Predicting Fracture Risk in Postmenopausal Women" *Osteoporosis International*, vol. 12, pp. 519-528 (2001).

Blake et al., "Active Contours; The Application of Techniques from Graphics, Vision, Control Theory and Statistics to Visual Tracking of Shapes in Motion," Title page and Table of Contents pages only, 6 pages (1999).

Bushberg et al., "The Essential Physics of Medical Imaging," Lipincott, Williams & Wilkins, Title page and Table of Contents pages only, 3 pages (1994).

Cann, "Quantitative CT for Determination of Bone Mineral Density: A Review," Radiology, vol. 166, No. 2, pp. 509-522 (1988).

Castleman, "Digital Image Processing," Prentice Hall, Title page and Table of Contents pages only, 9 pages (1996).

Cheal et al., "Role of Loads & Prosthesis Material Properties on the Mechanics of the Proximal Femur After Total Hip Arthroplasty," *J. Orthop. Res.*, vol. 10, No. 3, pp. 405-422 (1992).

Cootes et al., "Anatomical statistical models and their role in feature extraction," *The British Journal of Radiology*, Special Issue, 7 pages [S133-S139] (2004).

Cootes et al., "Statistical models of appearance for medical image analysis and computer vision," *Proc. SPIE Medical Imaging*, 14 pages, (2001).

Cootes, "An Introduction to Active Shape Models," *Image Processing and Analysis*, Ch. 7, pp. 1-26 (2000).

Cortet et al., "Bone Microarchitecture and Mechanical Resistance," *Joint Bone Spine*, vol. 68, pp. 297-305 (2001).

Crabtree et al., "Improving Risk Assessment: Hip Geometry, Bone Mineral Distribution and Bone Strength in Hip Fracture Cases and Controls. The EPOS Study," *Osteoporos Int*, vol. 13, pp. 48-54 (2002).

Crawley, "In Vivo Tissue Characterization Using Quantitative Computed Tomography: A Review," *Journal of Medical Engineering & Technology*, vol. 14, No. 6, pp. 233-242 (1990).

Cummings et al., "Bone Density at Various Sites for Prediction of Hip Fractures," *The Lancet*, vol. 341, pp. 72-75 (1993).

Davies et al., "A Minimum Description Length Approach to Statistical Shape Modeling," IEEE Transaction on Medical Imaging, vol. 21, No. 5, pp. 525-537 (2002).

Duryea et al., "New radiographic-based surrogate outcome measures for osteoarthritis of the knee," *Osteoarthritis and Cartilage*, vol. 11, pp. 102-110 (2003).

Duryea et al., "Trainable rule-based algorithm for the measurement of joint space width in digital radiographic images of the knee," *Medical Physics*, vol. 27, No. 3, pp. 580-591 (2000).

Eastell, "Treatment of Postmenopausal Osteoporosis," *New Engl. J. of Med.*, vol. 338, No. 11, pp. 736-746 (1988).

Engelman et al., "Impact of Geographic Barriers on the Utilization of Mammograms by Older Rural Women, "*Journal of the American Geriatrics Society*, vol. 50, No. 1, pp. 62-68 (2002).

Faulkner "Bone Densitometry: Choosing the Proper Skeletal Site to Measure," *J. Clin. Densitometry*, vol. 1, No. 3, pp. 279-285 (1998).

Fleute et al. "Incorporating a statistically based shape model into a system for computer-assisted anterior cruciate ligament surgery," Medical Image Analysis, vol. 3, No. 3, pp. 209-222 (1999).

Fleute et al., "Statistical model registration for a C-arm CT system," Computer Science Department, The Johns Hopkins University, pp. 1667-1670 (2002).

Fleute et al., "Nonrigid 3-D/2-D Registration of Images Using Statistical Models," pp. 138-147 (1999).

Geraets et al., "A New Method for Automatic Recognition of the Radiographic Trabecular Pattern," *J. Bone and Min Res.*, Department of Oral Radiology, Academic Center for Dentistry Amsterdam (ACTA), vol. 3, No. 3, pp. 227-233 (1990).

Gilliland et al., "Patterns of Mammography Use Among Hispanic, American Indian, and Non-Hispanic White Women in New Mexico, 1994-1997," *American Journal of Epidemiology*, vol. 152, No. 5, pp. 432-437 (2000).

Gluer et al., Peripheral Measurement Techniques for the Assessment of Osteoporosis, *Semin. Nucl. Med.*, vol. 27, No. 3, pp. 229-247 (1997).

Gluer, "Quantitative Ultrasound Techniques for the Assessment of Osteoporosis: Expert Agreement on Current Status," *J. Bone Miner. Res.*, vol. 12, No. 8, pp. 1280-1288 (1997).

Grisso et al., "Risk Factors for Falls as a Cause of Hip Fracture in Women. The Northeast Hip Fracture Study Group," *N. Engl. J. Med.*, (Abstract Page Only), 1 page, vol. 324, No. 19 (1991).

Gudmundsdottir et al., "Vertebral Bone Density in Icelandic Women Using Quantitative Computed Tomography Without an External Reference Phantom," *Osteoporosis Int.*, vol. 3, pp. 84-89 (1993).

Hayes et al., "Biomechanics of Cortical and Trabecular Bone: Implications for Assessment of Fracture Risk," *Basic Orthopaedic Biomechanics*, 2nd Ed., Ch. 3, pp. 69-111, Lippincott-Raven, publishers (1997).

Hayes et al., "Biomechanics of Fracture Risk Prediction of the Hip and Spine by Quantitative Computed Tomography," *Radiologic Clinics of North America*, vol. 29, No. 1, pp. 1-18 (1991).

Hayes et al., "Impact Near the Hip Dominates Fracture Risk in Elderly Nursing Home Residents Who Fall," *Calcif. Tissue Int.* (Abstract Page Only), 1 page, vol. 52, No. 3 (1993).

Hedström et al., "Biochemical Bone Markers and Bone Density in Hip Fracture Patients," *Acta Orthop. Scand.*, vol. 71, No. 4, pp. 409-413 (2000).

Horn, "Closed-form solution of absolute orientation using unit quaternions," *J. Opt. Soc. of Am. A*, vol. 4, No. 4, pp. 629-642 (1987).

Hosking et al., "Prevention of Bone Loss with Alendronate in Postmenopausal Women Under 60 Years of Age," *N. Engl. J. Med.*, vol. 338, No. 8, pp. 485-492 (1998).

Ikuta et al., "Quantitative Analysis Using the Star Volume Method Applied to Skeleton Patterns Extracted with a Morphological Filter," *Journal of Bone and Mineral Metabolism*, vol. 18, pp. 271-277 (2000).

Jacobs et al., "Long-term Bone Mass Evaluation of Mandible and Lumbar Spine in a Group of Women Receiving Hormone Replacement Therapy," *European Journal Oral Sciences*, vol. 104, pp. 10-16 (1996).

Jazieh et al., "Mammography Utilization Pattern Throughout the State of Arkansas: A Challenge for the Future," *Journal of Community Health*, vol. 26, No. 4, pp. 249-255 (2001).

Jeffcoat et al., "Post-menopausal bone loss and its relationship to oral bone loss", *Periodontology*, vol. 23, pp. 94-102 (2000).

Klose, "Teleradiology—A Model for Remote Consultation," *Electromedica*, vol. 66, No. 1, pp. 37-41 (1998).

Kumasaka et al., "Initial Investigation of Mathematical Morphology for the Digital Extraction of the Skeletal Characteristics of Trabecular Bone," *Dept. of Oral Surgery and Oral and Maxillofacial Radiology*, Kanagawa Dental College, Japan, pp. 161-168 (1996).

Lam et al., "X-Ray Diagnosis: A Physician's Approach," Title/Copyright pages and Index pages only, 4 pages, Springer-Verlag, publisher (ISBN 9813083247)(1998).

Lang et al., "Osteoporosis—Current Techniques and Recent Developments in Quantitative Bone Densitometry" *Radiologic Clinics of North America*, vol. 29, No. 1, pp. 49-76 (1991).

Marshall et al., "Meta-Analysis of How Well Measures of Bone Mineral Density Predict Occurrence of Osteoporotic Fractures," *Br. Med. J.*, vol. 312, pp. 1254-1259 (1996).

Metrabio Website, "QUS-2 Calcaneal Ultrasonometer," What's New: Ultrasound, Retrieved from the Internet—http://www.metrabio.com/html/_prods/L3-ultrasound-r.ht, 2 pages (2001).

Mourtada et al., "Curved Beam Model of the Proximal Femur for Estimating Stress Using Dual-Energy X-Ray Absorptiometry Derived Structural Geometry," *J. Ortho. Res.*, vol. 14, No. 3, pp. 483-492 (1996).

Njeh et al., "The Role of Ultrasound in the Assessment of Osteoporosis: A Review," *Osteoporosis Int.*, vol. 7, pp. 7-22 (1997).

Njeh et al., "Quantitative Ultrasound: Assessment of Osteoporosis and Bone Status," Title page and Table of Contents pages only, 4 pages (1999).

Ouyang et al., "Morphometric Texture Analysis of Spinal Trabecular Bone Structure Assessed Using Orthogonal Radiographic Projections," *Med. Phys.*, vol. 25, No. 10, pp. 2037-2045 (1998).

Patel et al., "Radiation Dose to the Patient and Operator from a Peripheral Dual X-Ray Absorptiometry System," *Journal of Clinical Densitometry*, vol. 2, No. 4, pp. 397-401 (1999).

Pharoah, "X-Ray Film, Intensifying Screens, and Grids," Ch. 4, Section 4: Imaging Principles and Techniques, Oral Radiology, $4^{th}$ ed., pp. 68-76 (2000).

Pinilla et al., "Impact Direction from a Fall Influences the Failure Load of the Proximal Femur as Much as Age-Related Bone Loss," *Calcified Tissue International*, vol. 58, pp. 231-235 (1996).

Riggs et al., "Changes in Bone Mineral Density of the Proximal Femur and Spine with Aging: Differences Between the Postmenopausal and Senile Osteoporosis Syndromes," *J. Clin. Invest.*, vol. 70, pp. 716-723 (1982).

Russ, "The Image Processing Handbook," $3^{rd}$ Edition, North Carolina State Univ., Chapter 7: Processing Binary Images, pp. 494-501 (1998).

Ruttiman et al. "Fractal Dimension from Radiographs of Peridontal Alveolar Bone: A Possible Diagnostic Indicator of Osteoporosis," *Oral Surg, Oral Med, Oral Pathol.*, vol. 74, No. 1, pp. 98-110 (1992).

Sandler et al. "An Analysis of the Effect of Lower Extremity Strength on Impact Severity During a Backward Fall," *Journal of Biomechanical Engineering*, vol. 123, pp. 590-598 (2001).

Shrout et al., "Comparison of Morphological Measurements Extracted from Digitized Dental Radiographs with Lumbar and Femoral Bone Mineral Density Measurements in Postmenopausal Women," *J. Periondontal*, vol. 71, No. 3, pp. 335-340 (2000).

Slone et al., "Body CT: A Practical Approach," Title page and Table of Contents pages only, 4 pages, McGraw-Hill, publisher (ISBN 007058219) (1999).

Southard et al., "Quantitative Features of Digitized Radiographic Bone Profiles," *Oral Surgery, Oral Medicine, and Oral Pathology*, vol. 73, No. 6, pp. 751-759 (1992).

Southard et al., "The Relationship Between the Density of the Alveolar Processes and that of Post-Cranial Bone," *J. Dent. Res.*, vol. 79, No. 4, pp. 964-969 (2000).

Stout et al., "X-Ray Structure Determination: A Practical Guide," 2nd Ed., Title page and Table of Contents pages only, 4 pages, John Wiley & Sons, publisher (ISBN 0471607118) (1989).

Svendsen et al., "Impact of Soft Tissue on In-Vivo Accuracy of Bone Mineral Measurements in the Spine, Hip, and Forearm: A Human Cadaver Study," *J. Bone Miner. Res.*, vol. 10, No. 6, pp. 868-873 (1995).

Tothill et al., "Errors due to Non-Uniform Distribution of Fat in Dual X-Ray Absorptiometry of the Lumbar Spine," *Br. J. Radiol.*, vol. 65, pp. 807-813 (1992).

Van den Kroonenberg et al., "Dynamic Models for Sideways Falls from Standing Height," *Journal of Biomechanical Engineering*, vol. 117, pp. 309-318 (1995).

Verhoeven et al., "Densitometric Measurement of the Mandible: Accuracy and Validity of Intraoral Versus Extraoral Radiographic Techniques in an In Vitro Study," *Clin. Oral Impl. Res.*, vol. 9, pp. 333-342 (1998).

White et al., "Alterations of the Trabecular Pattern in the Jaws of Patients with Osteoporosis," *Oral Surg., Oral Med., Oral Pathol., Oral Radiol., and Endod.*, vol. 88, pp. 628-635 (1999).

Yoshikawa et al., "Geometric Structure of the Femoral Neck Measured Using Dual-Energy X-Ray Absorptiometry," *J. Bone Miner. Res.*, vol. 10, No. 3, p. 510 (Abstract Only) (1995).

European Patent Office, European Supplementary Search Report—Application No. EP 03713907, dated Dec. 6, 2006 (3 pages).

European Patent Office, EPO Communication—Appl. No. 01 966 370.7-1224, dated Jun. 19, 2008 (4 pages).

European Patent Office, EPO Communication—Appl. No. 03 713 907.8-1240, dated Jun. 5, 2007 (6 pages).

European Patent Office, EPO Communication—Appl. No. 03 713 907.8-1240, dated Aug. 4, 2008 (4 pages).

European Patent Office, EPO Communication—Appl. No. 03 713 907.8-1240, dated Feb. 17, 2009 (5 pages).

International Searching Authority, International Preliminary Examination Report—Appl. No. PCT/US2001/026913, dated Aug. 12, 2003 (2 pages).

International Searching Authority, International Search Report—Appl. No. PCT/US2001/026913, dated May 21, 2003 (6 pages).

International Searching Authority, International Preliminary Examination Report—Appl. No. PCT/US2003/006692, dated Dec. 8, 2003 (3 pages).

International Searching Authority, International Search Report—Appl. No. PCT/US2003/006692, dated Sep. 23, 2003 (1 page).

International Searching Authority, International Preliminary Report on Patentability—Appl. No. PCT/US2005/028004, dated Feb. 13, 2007 (8 pages).

International Searching Authority, International Search Report—Appl. No. PCT/US2005/028004, dated Dec. 13, 2005 (2 pages).

International Searching Authority, Written Opinion of International Searching Authority—Appl. No. PCT/US2005/028004, dated Dec. 13, 2005 (7 pages).

United States Patent and Trademark Office, Non-Final Office Action—U.S. Appl. No. 09/942,528, dated Nov. 25, 2002 (17 pages).

Cooley Godward LLP Palo Alto, CA, Response to Non-Final Office Action—U.S. Appl. No. 09/942,528, filed Apr. 4, 2003 (17 pages).

United States Patent and Trademark Office, Non-Final Office Action—U.S. Appl. No. 09/942,528, dated Aug. 19, 2003 (15 pages).

Robins & Pasternak LLP Palo Alto, CA, Amendment to Non-Final Office Action—U.S. Appl. No. 09/942,528, filed Oct. 6, 2003 (13 pages).

United States Patent and Trademark Office, Final Office Action—U.S. Appl. No. 09/942,528, dated Nov. 24, 2003 (15 pages).

Robins & Pasternak LLP Palo Alto, CA, Response After Final and Request to Withdraw Finality to Final Office Action—U.S. Appl. No. 09/942,528, filed Jan. 22, 2004 (13 pages).

United States Patent and Trademark Office, Final Office Action—U.S. Appl. No. 09/942,528, dated Feb. 13, 2004 (16 pages).

Robins & Pasternak LLP Palo Alto, CA, Response After Final to Final Office Action—U.S. Appl. No. 09/942,528, filed Mar. 9, 2004 (9 pages).

Robins & Pasternak, LLP Palo Alto, CA, Request for Continued Examination to Final Office Action—U.S. Appl. No. 09/942,528, filed Jul. 1, 2004 (4 pages).

United States Patent and Trademark Office, Non-Final Office Action—U.S. Appl. No. 09/942,528, dated Jan. 24, 2005 (12 pages).

Kenyon & Kenyon San Jose, CA, Amendment and Response to Non-Final Office Action—U.S. Appl. No. 09/942,528, filed May 24, 2005 (21 pages).

United States Patent and Trademark Office, Final Office Action—U.S. Appl. No. 09/942,528, dated Sep. 6, 2005 (14 pages).

Kenyon & Kenyon San Jose, CA Request for Reconsideration Accompanied by Amendment to Final Office Action—Appl. No. 09/942,528, filed Jan. 6, 2006 (13 pp.).

Bromberg & Sunstein LLP Boston, MA, Request for Continued Examination Accompanied by Amendment to Final Office Action and Advisory Action—U.S. Appl. No. 09/942,528, filed Sep. 25, 2006 (12 pages).

United States Patent and Trademark Office, Non-Final Office Action—U.S. Appl. No. 09/942,528, dated Feb. 20, 2007 (12 pages).

Bromberg & Sunstein LLP Boston, MA, Amendment to Non-Final Office Action—U.S. Appl. No. 09/942,528, filed May 21, 2007 (11 pages).

United States Patent and Trademark Office, Final Office Action—U.S. Appl. No. 09/942,528, dated Aug. 8, 2007 (12 pages).

Bromberg & Sunstein LLP Boston, MA, Amendment Accompanying Request for Continued Examination to Final Office—U.S. Appl. No. 09/942,528, filed Oct. 30, 2007 (12 pages).

United States Patent and Trademark Office, Non-Final Office Action—U.S. Appl. No. 09/942,528, dated Nov. 27, 2007 (13 pages).

Bromberg & Sunstein LLP Boston, MA, Response to Non-Final Office Action—U.S. Appl. No. 09/942,528, filed May 22, 2008 (11 pages).

United States Patent and Trademark Office, Non-Final Office Action—U.S. Appl. No. 10/086,653, dated Mar. 2, 2004 (17 pages).

Robins & Pasternak LLP Palo Alto, CA, Amendment to Non-Final Office Action—Appl. No. 10/086,653, filed Sep. 1, 2004 (19 pages).

United States Patent and Trademark Office, Notice of Non-Compliant Amendment—U.S. Appl. No. 10/086,653, dated Sep. 17, 2004 (2 pages).

Robins & Pasternak LLP Palo Alto, CA, Amendment in Response to Notice of Non-Compliant Amendment—U.S. Appl. No. 10/086,653, filed Oct. 8, 2004 (20 pages).

United States Patent and Trademark Office, Notice of Non-Compliant Amendment—U.S. Appl. No. 10/086,653, dated Nov. 10, 2004 (2 pages).

Robins & Pasternak LLP Palo Alto, CA, Amendment in Response to Notice of Non-Compliant Amendment—U.S. Appl. No. 10/086,653, filed Dec. 17, 2004 (22 pages).

United States Patent and Trademark Office, Non-Final Office Action—U.S. Appl. No. 10/225,363, dated Mar. 2, 2004 (17 pages).

Robins & Pasternak LLP Palo Alto, CA, Amendment to Non-Final Office Action—U.S. Appl. No. 10/225,363, filed Aug. 4, 2004 (20 pages).

United States Patent and Trademark Office, Final Office Action—U.S. Appl. No. 10/225,363, dated Oct. 20, 2004 (12 pages).

Kenyon & Kenyon San Jose, CA, Amendment and Request for Continued Examination (RCE) to Final Office Action —U.S. Appl. No. 10/225,363, filed Jan. 21, 2005 (23 pages).

United States Patent and Trademark Office, Non-Final Office Action—U.S. Appl. No. 10/225,363, dated Apr. 14, 2005 (12 pages).

Kenyon & Kenyon San Jose, CA, Amendment to Non-Final Office Action—U.S. Appl. No. 10/225,363, filed Jul. 14, 2005 (16 pages).

United States Patent and Trademark Office, Non-Final Office Action—U.S. Appl. No. 10/225,363, dated Aug. 3, 2005 (11 pages).

Kenyon & Kenyon San Jose, CA, Amendment to Non-Final Office Action—U.S. Appl. No. 10/225,363, filed Dec. 5, 2005 (23 pages).

United States Patent and Trademark Office, Non-Final Office Action—U.S. Appl. No. 10/917,848, dated Dec. 2, 2005 (12 pages).

Kenyon & Kenyon LLP San Jose, CA 95110, Amendment to Non-Final Office Action—U.S. Appl. No. 10/917,848, filed Mar. 1, 2006 (10 pages).

United States Patent and Trademark Office Non-Final Office Action—U.S. Appl. No. 10/917,848, dated Sep. 22, 2006 (9 pages).

Bromberg & Sunstein LLP Boston, MA, Response to Non-Final Office Action—U.S. Appl. No. 10/917,848, filed Mar. 22, 2007 (8 pages).

United States Patent and Trademark Office, Final Office Action—U.S. Appl. No. 10/917,848, dated Jun. 4, 2007 (13 pages).

Bromberg & Sunstein LLP Boston, MA, Response with Request for Continued Examination to Final Office Action—U.S. Appl. No. 10/917,848, filed Oct. 30, 2007 (12 pages).

United States Patent and Trademark Office, Non-Final Office Action—U.S. Appl. No. 12/055,491, dated Jul. 29, 2008 (8 pages).

Bromberg & Sunstein LLP Boston, MA, Amendment to Non-Final Office Action—U.S. Appl. No. 12/055,491, filed Jan. 29, 2009 (18 pages).

United States Patent and Trademark Office, Notice of Non-Compliant Amendment—U.S. Appl. No. 12/055,491, dated Feb. 17, 2009 (2 pages).

Bromberg & Sunstein LLP Boston, MA, Response to Notice of Non-Compliant Amendment—U.S. Appl. No. 12/055,491, filed Mar. 11, 2009 (8 pages).

* cited by examiner

Sacle: 2:1

| ITEM NO. | PARTY NUMBER | QTY. |
|---|---|---|
| 1 | Bottom Laminated Plastic-V01 | 1 |
| 2 | Top Laminated Plastic-V01 | 1 |
| 3 | Copper Strip-V01 | 1 |

<u>ASSEMBLY NOTES</u>

1. LAMINATE COPPER PARTS BETWEEN TWO (2) 0.012" THICK PLASTIC LAYERS AS SHOWN

2"
Scale: 2:1

0.625"+0.0005"

SCALE 2:1
Hip X-ray Aluminum
Calivration Device

Material: Alloy 2024 Precision Ground Aluminum Rod 5/8" ASTM B211/221

CALIBRATION DEVICES AND METHODS OF USE THEREOF

CROSS-REFERENCE TO RELATED APPLICATIONS

This application is a continuation of U.S. Ser. No. 12/055,491, filed Mar. 26, 2008, which in turn is a continuation of U.S. Ser. No. 10/917,848, filed Aug. 12, 2004, issued as U.S. Pat. No. 7,467,892, which in turn is a continuation-in-part of U.S. Ser. No. 10/225,363, filed Aug. 20, 2002, issued as U.S. Pat. No. 7,050,534, which in turn is a continuation-in-part of U.S. Ser. No. 10/086,653, filed Feb. 27, 2002, issued as U.S. Pat. No. 6,904,123, which in turn is a continuation-in-part of U.S. Ser. No. 09/942,528, filed Aug. 29, 2001, issued as U.S. Pat. No. 7,545,964, which in turn claims the benefit of U.S. Provisional Patent Application Ser. No. 60/228,591, filed Aug. 29, 2000, all of which applications are incorporated herein by reference in its entirety.

TECHNICAL FIELD

The present invention is in the field of radiographic imaging and analysis thereof. In particular, calibration phantoms and methods of using these calibration phantoms are described.

BACKGROUND

X-rays and other radiographic analysis are important diagnostic tools. In order to rely on data extracted from radiographs, it is often helpful to include a phantom of known radiopacity. Calibration references (also known as calibration phantoms) for use in imaging technologies have also described. See, e.g., U.S. Pat. No. 5,493,601 and U.S. Pat. No. 5,235,628. U.S. Pat. No. 5,335,260 discloses a calibration phantom representative of human tissue containing variable concentrations of calcium that serves as reference for quantifying calcium, bone mass and bone mineral density in radiography and CT imaging systems. However, currently-available calibration phantoms are not always accurate, due to both the effect of structures or materials that project on or with the calibration phantom and, additionally, to the fact that one or more regions of the calibration phantom do not always appear on the x-ray image.

Thus, there remains a need for calibration devices that provide references for density and geometry of the images structures.

SUMMARY

The present invention meets these and other needs by providing compositions and methods that allow for calibration of density and/or geometry data obtained from radiographs, particularly x-rays.

In one aspect, a calibration device comprising a radiopaque material (e.g., copper or aluminum) having a stepped thickness is described. In certain embodiments, the step-wedge calibration device has equivalent bone area density coverage ranging from about 0.02 g/cm$^2$ to about 1.5 g/cm$^2$ (this range having a coefficient of variation of less than about 10%). Any of the step-wedges described herein may include one or more clear coverings on one more sides, for example a plastic laminate (e.g., approximately 0.012 inches thickness) on either side of the step-wedge.

In another aspect, a calibration device comprising a radiopaque material (e.g., copper or aluminum) in a rod-shape is described. In certain embodiments, the rod-shaped calibration device has an optical density of between about 30% and about 70% of the optical density range covered by a step-wedge as described herein, when imaged with energy between about 70 kVp and 80 kVp (this range having a coefficient of variation of less than about 10%).

In another aspect, the calibration device comprises any of the step-wedge calibration devices described herein in combination with any of the rod-shaped calibration devices described herein. The step-wedge and rod may be permanently or temporarily attached to each other, for example using a plastic laminate to align the calibration devices such that the long axis of the rod is parallel to the long axis of each rectangle making up the step-wedge.

In another aspect, methods of using any of the calibration devices described herein, alone or in combination, are described. In certain embodiments, the methods comprise obtaining an x-ray image of hip comprising one or more calibration devices as described herein. In certain embodiments, the method of obtaining a hip x-ray of a patient comprises the steps of centering the central ray to femoral neck; placing one or more calibration devices as described herein with the center label aligned with transverse line of aiming cross placing a film cassette in bucky tray; centering the film cassette to central ray; adjusting width of collimator to include all of the calibration device in exposure field; rotating the patient's leg internally 15-20 degrees; and producing an x-ray image of the patient's hip. In certain embodiments, the x-ray image is produced using a current of 150 mA, energy of 70 kV to 80 kV, using an automatic exposure time, a 400 speed screen and a source height of approximately 40 inches (102 cm). In any of the methods described herein, the film size may be 14"×11" (36 cm×28 cm). Furthermore, the leg may be held in place by the use of blocks and/or straps.

Another aspect of the invention is a kit for aiding in assessing the condition of bone in a subject, which kit comprises a software program and one or more calibration devices as described herein. When installed and executed on a computer reads an x-ray image (e.g. a digital or digitized dental x-ray) comprising the calibration device(s) and produces a computer readout showing bone mineral density and/or bone structure. Any of the kits described herein can also include an x-ray film, x-ray film holders and computer programs (e.g., software) for displaying and/or generating a bill for the readout regarding bone mineral density.

In yet another aspect, methods of diagnosing osteoporosis in a subject are provided, for example using any of the kits, methods and/or devices described herein. In certain embodiments, the methods of diagnosing osteoporosis in a subject comprise using a computer program to analyze bone mineral density and/or bone structure of an x-ray image and comparing the bone mineral density and/or bone structure data obtained from the image with a reference standard or curve, thereby determining if the subject has osteoporosis. In certain embodiments, the x-ray image includes a calibration phantom, for example a calibration phantom as described herein. In other embodiments, a reference calibration curve can be used to analyze the image.

In still further aspects, methods of assessing bone mineral density and/or bone structure are used to provide suitable treatment for a subject in need thereof. For instance, using any of the methods, kits, and/or devices described herein, the presence of osteoporosis in a subject can be diagnosed and that subject provided with appropriate therapy (e.g., one or more anti-resorptive agents and/or one or more anabolic agents).

BRIEF DESCRIPTION OF THE FIGURES

FIG. 1A is a top view depicting dimensions of each of the rectangles making up the step-wedge. FIG. 1B is a perspective view. FIG. 1C is side view and depicts the thickness of each rectangle making up the step-wedge.

FIG. 2A depicts positioning of the step-wedge between two plastic sheets. FIG. 2B depicts the dimensions of the plastic covering and overall device. FIG. 2C is a perspective view depicting a laminated step-wedge calibration device suitable for use in hip x-ray imaging.

DETAILED DESCRIPTION

Figure 1A:
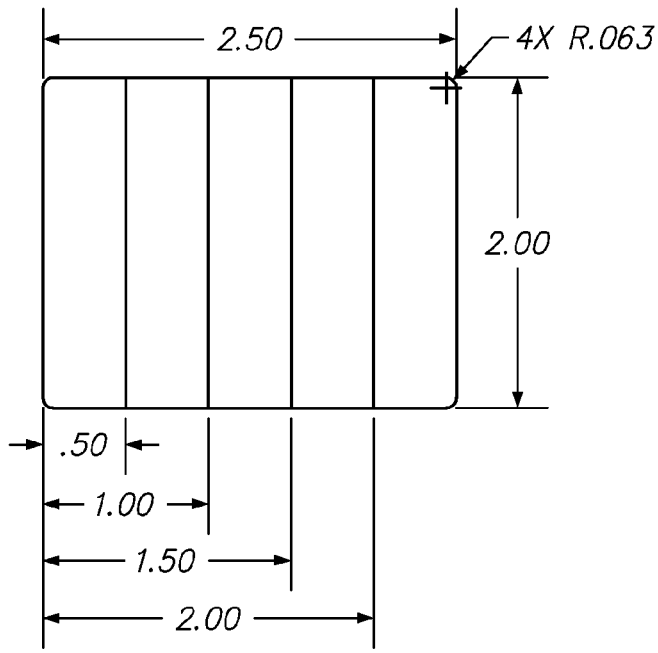
FIGS. 1A-C, depict an exemplary step-wedge calibration device of the present invention.

The following description is presented to enable any person skilled in the art to make and use the invention. Various modifications to the embodiments described will be readily apparent to those skilled in the art, and the generic principles defined herein can be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. To the extent necessary to achieve a complete understanding of the invention disclosed, the specification and drawings of all issued patents, patent publications, and patent applications cited in this application are incorporated herein by reference.

As will be appreciated by those of skill in the art, methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The practice of the present invention employs, unless otherwise indicated, conventional methods of database storage and manipulation, within the skill of the art. Such techniques are explained fully in the literature. See, e.g., Numerical Mathematical Analysis, Third Edition, by J. B. Scarborough, 1955, John Hopkins Press, publisher; System Analysis and Design Methods, by Jeffrey L. Whitten, et al., Fourth Edition, 1997, Richard D. Irwin, publisher; Modern Database Management, by Fred R. McFadden, et al., Fifth Edition, 1999, Addison-Wesley Pub. Co., publisher; Modern System Analysis and Design, by Jeffery A. Hoffer, et al., Second Edition, 1998, Addison-Wesley Pub. Co., publisher; Data Processing: Fundamentals, Design, and Implementation, by David M. Kroenke, Seventh Edition, 2000, Prentice Hall, publisher; Case Method: Entity Relationship Modelling (Computer Aided Systems Engineering), by Richard Barker, 1990, Addison-Wesley Pub Co., publisher.

General Overview

Methods and compositions useful in analyzing x-ray images are described. In particular, the invention includes methods of obtaining and/or deriving information from an x-ray image in network environment. Additionally, the present invention relates to the provision of accurate calibration phantoms for X-ray systems and methods of using these calibration phantoms. Typically, the calibration phantom is formed of a material that simulates the properties of human bone tissue and is provided in an x-ray assembly such that improved accuracy and precision in the quantification of calcium, bone mass and bone density using conventional X-ray equipment is achieved.

Calibration Devices

Although a wealth of information can be obtained from radiographic images alone, it is highly preferred that the images include one or more accurate reference markers, for example calibration phantoms for assessing density and geometry of any given structure in any given image. Geometry refers broadly to any bone structure parameter, for example as described in U.S. Ser. No. 10/809,578, incorporated by reference herein in its entirety.

Thus, in certain aspects, the current invention provides for methods and devices (e.g. a comparison device 520 and an estimation device 530, FIG. 5C) that allow accurate quantitative assessment of information contained in an image such as density, geometry or morphology of an anatomic structure.

The calibration phantom materials and methods of the present invention are suitable for use in both conventional radiography systems and computed tomography (CT) systems. In conventional radiography systems, for example, a step-wedge phantom can be fabricated from a matrix containing a desired concentration of reference material in varying thicknesses is used. In certain embodiments, the image is an x-ray image, for example of hip, spine, knee, ankle, elbow, etc. X-ray images can be acquired using well-known techniques from any local site. For example, in certain aspects, 2D planar x-ray imaging techniques are used. 2D planar x-ray imaging is a method that generates an image by transmitting an x-ray beam through a body or structure or material and by measuring the x-ray attenuation on the other side of said body or said structure or said material. 2D planar x-ray imaging is distinguishable from cross-sectional imaging techniques such as computed tomography or magnetic resonance imaging.

X-ray images that are captured using conventional x-ray film can be digitized using any suitable scanning device. The digitized x-ray image may then transmitted over the network, e.g. the Internet, into a remote computer or server. It will be readily apparent that x-ray images can also be acquired using digital acquisition techniques, e.g. using phosphorus plate systems or selenium or silicon detector systems, the x-ray image information is already available in digital format. In this case the image can be transmitted directly over the network, e.g. the Internet, or alternatively, it can be compressed prior to transmission.

In preferred embodiments, when an x-ray of an anatomic structure or a non-living object is acquired one or more calibration devices are included in the field of view. Any suitable calibration phantom can be used, for example, one that comprises aluminum, copper and/or other radiopaque materials. U.S. Pat. No. 5,335,260 describes other calibration phantoms suitable for use in assessing bone mineral density in x-ray images. Examples of other suitable calibration reference materials can be fluid or fluid-like materials, for example, one or more chambers filled with varying concentrations of calcium chloride or the like.

It will be readily apparent that a calibration phantom can contain several different areas of different radiopacity. For example, the calibration phantom can have a step-like design, whereby changes in local thickness of the wedge result in differences in radiopacity. Stepwedges using material of varying thickness are frequently used in radiology for quality control testing of x-ray beam properties. By varying the thickness of the steps, the intensity and spectral content of the x-ray beam in the projection image can be varied. Stepwedges are commonly made of aluminum, copper and other convenient and homogeneous materials of known x-ray attenuation properties. Stepwedge-like phantoms can also contain calcium phosphate powder or calcium phosphate powder in molten paraffin.

Figure 1B:
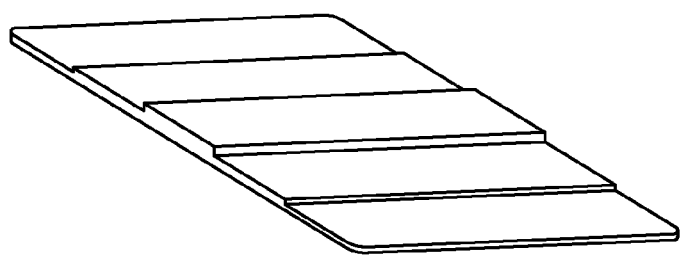
Figure 1C:
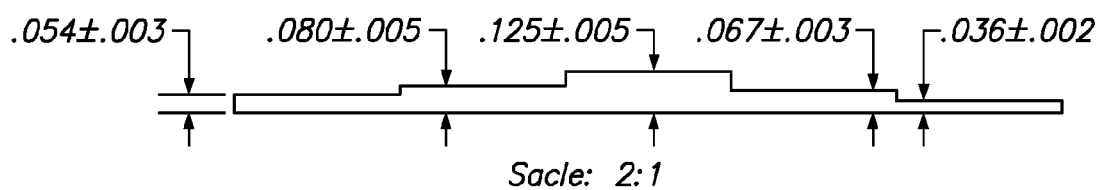

FIG. 1, panels A-C, shows an exemplary step-wedge calibration phantom according to the present invention. Dimensions are shown in inches unless other specified. Panel (A) shows a top view and the overall dimensions as well as the distance between wedges (6 wedges shown in FIG. 1). Each rectangle of the step-wedge is approximately 0.5 inch long. Panel (B) shows a perspective view and Panel (C) shows a side view and depicts dimensions of the stepped nature of the phantom. The dimensions (e.g., height) of each component of the step-wedge is shown between the arrows, in a 2:1 scale. One of skill in the art will recognize that the shape and specific dimensions of the phantom shown in FIG. 1 are exemplary (e.g., for hip x-rays) and can be varied according to the teachings herein. For instances in which the calibration phantom is to be used in smaller x-rays (e.g., dental x-rays), the device will be smaller. In one preferred embodiment, the step-wedge calibration phantom comprises copper.

Figure 2A:
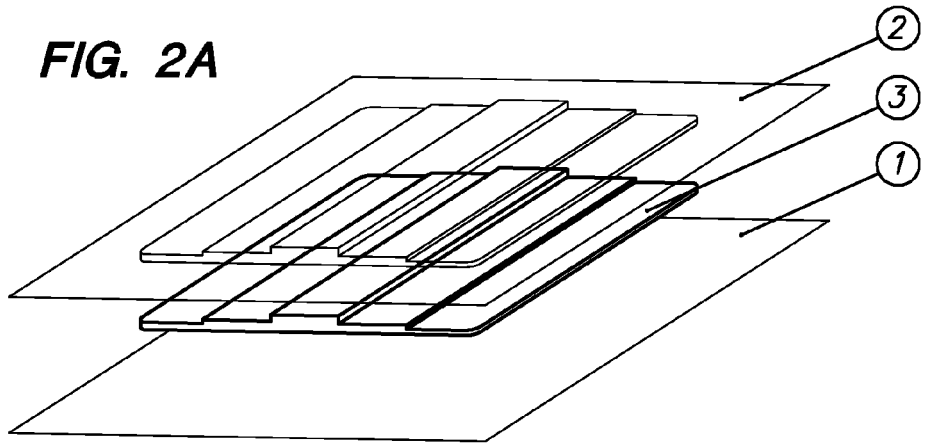
FIGS. 2A-C depict lamination of the exemplary step-wedge calibration device of FIG. 1 between two clear plastic sheets.
Figure 2B:
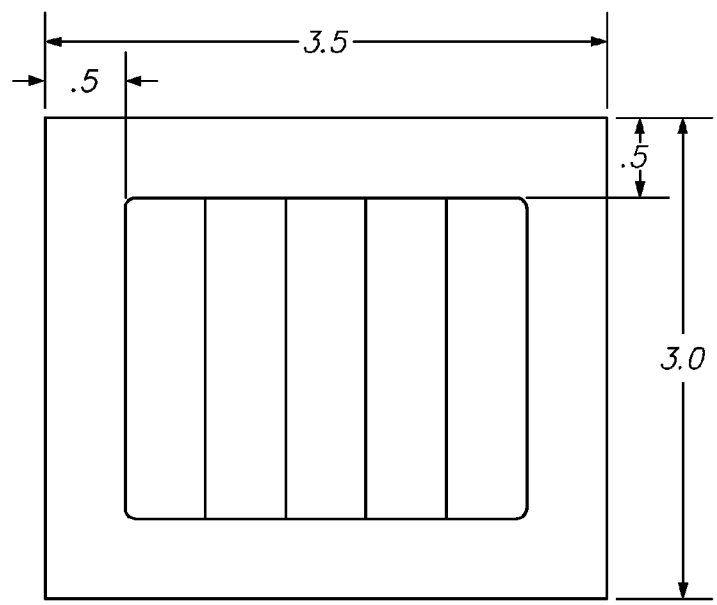
Figure 2C:
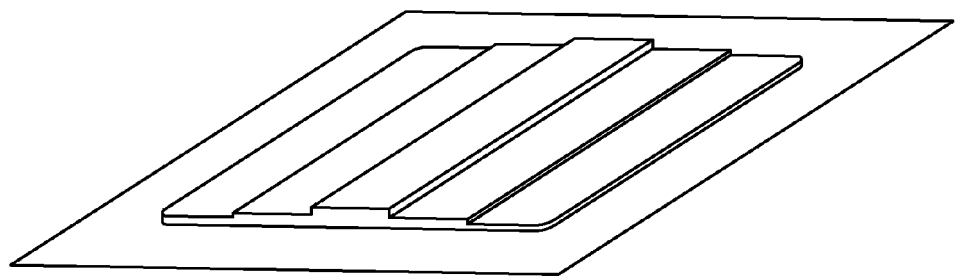

FIGS. 2A-C shows lamination of an exemplary copper step-wedge as described herein between to plastic layers. The thickness of the plastic is preferably such that it does not significantly effect imaging of the wedge. For example, as shown in FIG. 2, each plastic sheet may be approximately 0.012 inches thick.

Figure 3:
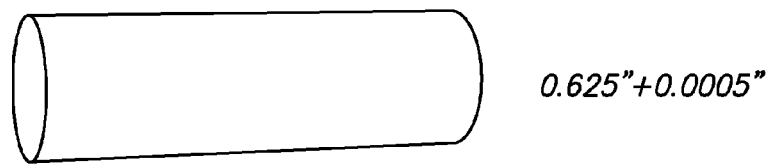
FIG. 3 is a perspective view depicting an exemplary rod-shaped calibration device.

FIG. 3 shows another exemplary embodiment of the present invention comprising a rod-shaped calibration device. The dimensions and characteristics of the exemplary device are shown in FIG. 3 and described in Example 1 below.

The calibration devices described herein may be reused and do not require sterilization prior to use. The calibration devices are typically re-useable for at least 6 months.

Figure 4:
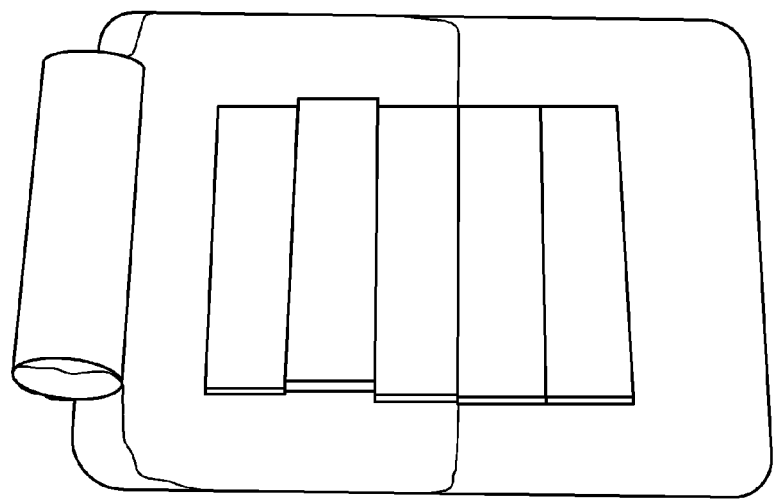
FIG. 4 is a perspective view depicting an exemplary combination calibration device as described herein comprising step-wedge and rod-shaped calibration devices.

In yet other embodiments, calibration devices as described herein may be combined to further enhance the accuracy of the data obtained from the radiograph. For example, as shown in FIG. 4, a step-wedge can be permanently attached to a rod-shaped calibration device. FIG. 4 depicts the device of FIG. 2C (laminated step-wedge) in combination with the device depicted in FIG. 3. In one preferred embodiment, the rod-shaped calibration device is affixed to the edge of the plastic laminate of the step-wedge such that the long axis of the rod is parallel to the long axis of the rectangles making up the step-wedge.

Since the density and attenuation of the calibration phantom are both known, the calibration phantom provides an external reference for measuring the density of the anatomic structure or non-living object to be measured.

Preferably, the calibration phantom can be imaged at the same time as the x-ray image. The calibration phantom can be physically connected to an x-ray film and/or film holder. Such physical connection can be achieved using any suitable mechanical or other attachment mechanism, including but not limited to adhesive, a chemical bond, use of screws or nails, welding, a Velcro™ strap or Velcro™ material and the like. Similarly, a calibration phantom can be physically connected to a detector system or a storage plate for digital x-ray imaging using one or more attachment mechanisms (e.g., a mechanical connection device, a Velcro™ strap or other Velcro™ material, a chemical bond, use of screws or nails, welding and an adhesive).

The attachment may be permanent or temporary and the calibration phantom can be integral (e.g., built-in) to the film, film holder and/or detector system or can be attached or positioned permanently or temporarily appropriately after the film and/or film holder is produced, whether integrally formed or not. Thus, the calibration phantom can be designed for single-use (e.g., disposable) or for multiple uses with different x-ray images. Thus, in certain embodiments, the calibration phantom is reusable and, additionally, can be sterilized between uses. Integration of a calibration phantom can be achieved by including a material of known x-ray density between two of the physical layers of the x-ray film. Integration can also be achieved by including a material of known x-ray density within one of the physical layers of the x-ray film. Additionally, the calibration phantom can be integrated into the film cover. A calibration phantom or an external standard can also be integrated into a detector system or a storage plate for digital x-ray imaging. For example, integration can be achieved by including a material of known x-ray density between two of the physical layers of the detector system or the storage plate. Integration can also be achieved by including a material of know x-ray density within one of the physical layers of the detector system or the storage plate.

In certain embodiments, for example those embodiments in which the calibration phantom is temporarily attached to the x-ray assembly, cross-hairs, lines or other markers may be placed on the apparatus as indicators for positioning of the calibration phantom. These indicators can help to ensure that the calibration phantom is positioned such that it doesn't project on materials that will alter the apparent density in the resulting image.

Methods

Any of the calibration phantom-containing assemblies described herein can be used in methods of analyzing and/or quantifying density and/or geometry of a structure in an x-ray image. The methods generally involve simultaneously imaging or scanning the calibration phantom and another material (e.g., bone tissue from a subject) for the purpose of quantifying the density or geometry of the imaged material (e.g., bone mass).

Thus, under the method of the present invention, a calibration phantom is preferably imaged or scanned simultaneously with the individual subject, although the invention allows for non-simultaneous scanning of the phantom and the subject. Methods of scanning and imaging structures by radiographic technique are well known. By placing the calibration phantom in the x-ray beam with the subject, reference calibration samples allow corrections and calibration of the absorption properties of bone. When the phantom is imaged or scanned simultaneously with each subject, the variation in x-ray beam energy and beam hardening are corrected since the phantom and the subject both see the same x-ray beam spectrum. Each subject, having a different size, thickness, muscle-to-fat ratio, and bone content, attenuate the beam differently and thus change the effective x-ray beam spectrum. It is necessary that the bone-equivalent calibration phantom be present in the same beam spectrum as the subject's bone to allow accurate calibration.

Figure 5A:
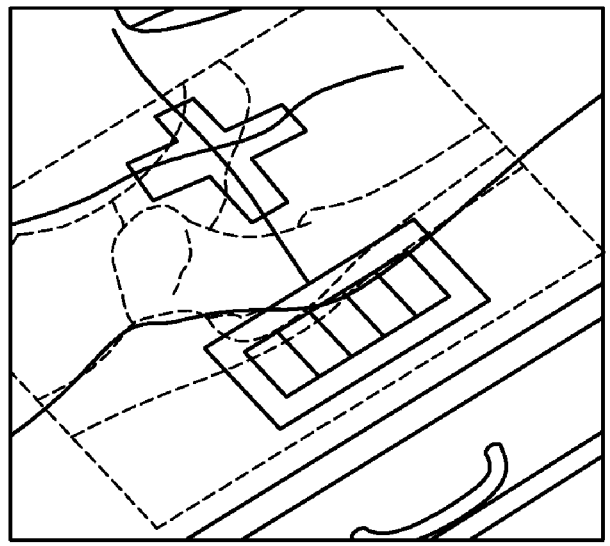
FIGS. 5A and B depict alignment of the bone, film and calibration device.
Figure 5B:
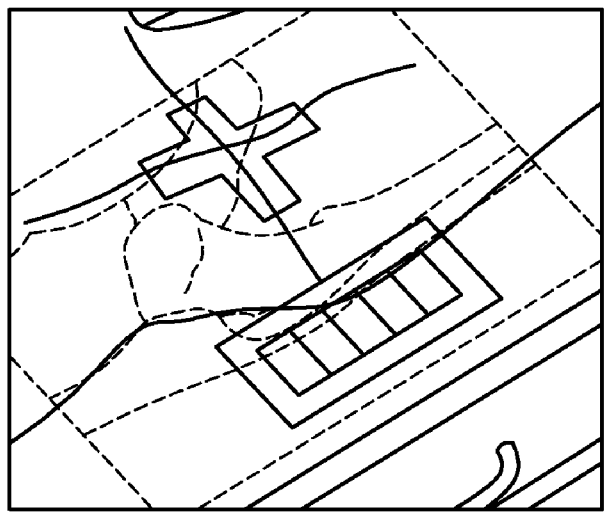
FIG. 5, panels A-C, depict selected steps in producing an x-ray image including a calibration device as described herein of a patient's hip.
FIG. 5C depicts positioning of the patient's leg and production of the x-ray image.
Figure 5C:
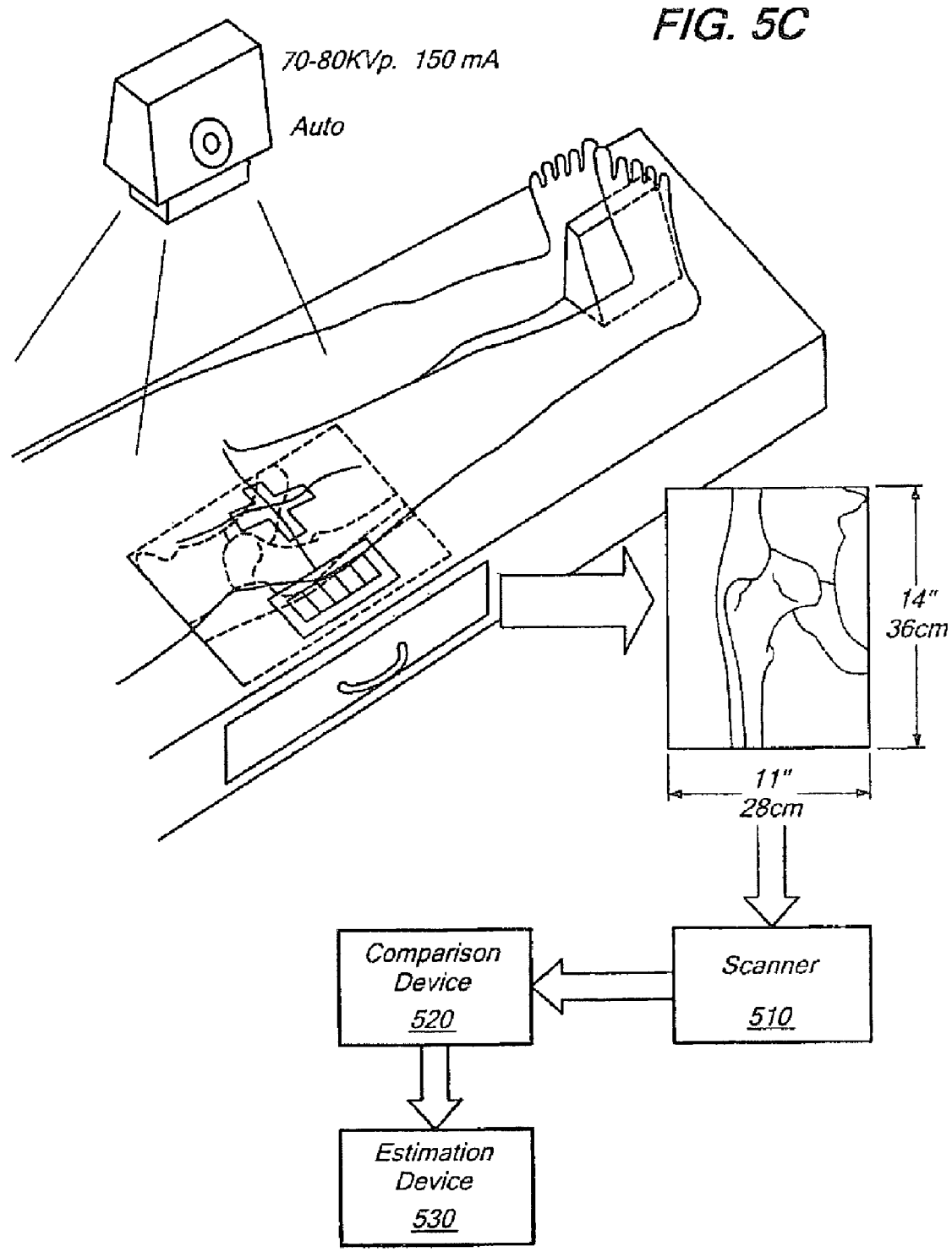

FIGS. 5A-C depict an exemplary method of using a calibration phantom as described herein to produce an x-ray image. FIG. 5A shows alignment of the central ray with the femoral neck (top arrow) as well as alignment of the center of the calibration device along the transverse line of aiming cross (bottom arrow). FIG. 5B depicts placement of a film cassette in a bucky tray and the film centered to central ray and adjusted width of collimator to include all of calibration device in exposure field. As shown in FIG. 5C, the x-ray is then taken after the patient's leg has been rotated 15-20 degrees internally and held in the rotated position. Exemplary x-ray conditions and parameters are also shown in FIG. 5C and described in Example 2 below.

In addition, the data obtained from the calibration device(s) (e.g., density and/or geometry) can be further manipulated. For example, one or more calibration curves can be constructed as described for example in International Publications WO 02/30283; WO 03/071934 and WO 04/019256, which disclosures are incorporated herein in their entireties.

Kits

The invention also provides kits for obtaining information from x-ray images, for example for obtaining information regarding bone mineral density from an x-ray. In certain embodiments, the kit comprises one or more computer (e.g., software) programs, for example for receiving, analyzing and generating reports based on x-ray images. In further embodiments, the kits can include calibration phantoms, for example calibration phantoms integrated or attachable-to x-ray film and/or x-ray film holders.

All of these aspects of the invention can be practiced separately or in combination. Typically, the use of combinations of the embodiments listed above is more advantageous. Further, although preferred embodiments of the subject invention have been described in some detail, it is understood that obvious variations can be made without departing from the spirit and the scope of the invention.

EXPERIMENTAL

Below are examples of specific embodiments for carrying out the present invention. The examples are offered for illustrative purposes only, and are not intended to limit the scope of the present invention in any way.

Example 1

Calibration Devices

A. Copper Stepped-Wedge

A step-wedge comprising copper was made as shown in FIG. 1. Dimensions of the step-wedge are shown in FIGS. 1 and 2. The device had equivalent area bone density coverage range of 0.02 g/cm$^2$ to 1.5 g/cm$^2$ and this bone density measurement had a variation of less than 10%. The step-wedge was laminated in plastic.

B. Aluminum Calibration Device

A calibration device made of aluminum was constructed as follows. Aluminum was selected because it has an x-ray attenuation coefficient similar to that of human cortical bone. A rod-shaped aluminum calibration device having the dimensions shown in FIG. 3 was constructed using standard techniques.

The aluminum device had an optical density between about 30% to 70% when imaged with energy between 70 kVp to 80 kVp. This optical density measurement had a coefficient of variation of less than 10%.

C. Combination Devices

The copper step-wedge and aluminum rod described above were combined into a single calibration device as follows. Using clear plastic sheets the aluminum rod was attached to the previously-laminated step-wedge such that the long axis of the aluminum rod was essentially parallel to the rectangles making up the step-wedge. FIG. 4.

Since the x-ray attenuation coefficient of copper decreases more rapidly with higher x-ray energy than that of aluminum, the x-ray energy used to capture an image can be estimated by comparing the optical density of the aluminum device to that of the copper device.

By providing a mechanism to estimate the x-ray energy, a more accurate attenuation coefficient of the copper calibration device is used to generate a more accurate standard calibration curve adjusted for the x-ray energy.

Example 2

Use of Calibration Device in Hip X-Rays

A calibration device as described in Example 1 (copper step-wedge or combination copper step-wedge-aluminum calibration device) was placed on the x-ray table, lengthwise, lateral, and adjacent to the patient with center of device aligned with the transverse aiming cross of collimator light. The central ray was centered with respect to the femoral neck and the calibration device was placed with the center is aligned with the transverse line of aiming cross. (FIG. 5A).

Subsequently, the film cassette was placed in the busky tray and centered to the central ray. The width of the collimator was adjusted to include all of the calibration device in the exposure field. (FIG. 5B). The patient's leg was then rotated internally 15-20 degrees using foam block and Velcro to maintain positioning. (FIG. 5C)

An x-ray image was created using the following parameters:

| | |
|---|---|
| Current | 150 mA |
| Energy | 70 kV-80 kV |
| Exposure time | Auto |
| Film size | 14" × 11" (36 cm × 28 cm) |
| Screen | 400 speed |
| Source height | 40" (102 cm) |

For images including the combination device, the x-ray energy used to capture an image was estimated by comparing the optical density of the aluminum device to that of the copper device.

The instant invention is shown and described herein in what is considered to be the most practical, and preferred embodiments. It is recognized, however, that departures may be made there from, which are within the scope of the invention, and that obvious modifications will occur to one skilled in the art upon reading this disclosure.

What is claimed is:
1. A system for image analysis, the system comprising:
at least one calibration phantom including a first material and a second material, the first material having an x-ray attenuation coefficient that decreases more rapidly with higher x-ray energy than the second material;

means for generating a radiographic image comprising the at least one calibration phantom;

means for comparing the optical density of the first and second material in the image; and means for estimating at least one image acquisition parameter based on the comparison.

2. The system of claim 1, wherein the means for generating is configured to use a current of 150 mA, energy of 70 kV to 80 kV, an automatic exposure time, a 400 speed screen and a source height of approximately 40 inches (102 cm).

3. The system according to claim 1, wherein the at least one image acquisition parameter estimated is the x-ray energy used to capture the image.

4. The system according to 3, further comprising means for determining a calibration curve adjusted for the estimated x-ray energy.

5. The system according to claim 1, wherein the first material is copper and the second material is aluminum.

6. The system according to claim 1, wherein the at least one calibration phantom includes a radiopaque step-wedge and a radiopaque rod.

7. The system according to claim 6, wherein the step-wedge includes rectangular steps having a long axis, wherein the rod has a long axis, and wherein the long axis of the rod and the rectangular steps are parallel.

8. The system according to claim 1, wherein the image further includes bone, the system further comprising means for deriving information on density or structure of bone from the image using the at least one calibration phantom.

9. A computer program product for use on a computer system for analyzing an image that includes at least one calibration phantom having a first material and a second material, the first material having an x-ray attenuation coefficient that decreases more rapidly with higher x-ray energy than the second material, the computer program product comprising a computer usable medium having computer readable program code thereon, the computer readable program code comprising:

program code for comparing the optical density of the first and second material in the image; and program code for estimating at least one image acquisition parameter based on the comparison.

10. The computer program product according to claim 9, wherein the program code for estimating at least one image acquisition parameter includes program code for estimating x-ray energy used to capture the image.

11. The computer program product according to claim 10, further comprising program code for determining a calibration curve adjusted for the estimated x-ray energy.

12. The computer program product according to claim 9, wherein the program code for comparing the optical density of the first and second material includes program code for comparing the optical density of copper and aluminum.

13. The computer product according to claim 9, wherein the image further includes bone, the computer product further comprising program code for deriving information on density or structure of bone from the image using the at least one calibration phantom.

14. A method of analyzing an x-ray, the method comprising the steps of:

obtaining a radiographic image comprising at least one calibration phantom, the at least one calibration phantom including a first material and a second material, the first material having an x-ray attenuation coefficient that decreases more rapidly with higher x-ray energy than the second material;

comparing the optical density of the first and second material in the image; and estimating at least one image acquisition parameter based on the comparison.

15. The method according to claim 14, wherein the at least one image acquisition parameter estimated is the x-ray energy used to capture the image.

16. The method according to claim 15, further comprising determining a calibration curve adjusted for the estimated x-ray energy.

17. The method according to claim 14, wherein the first material is copper and the second material is aluminum.

18. The method according to claim 14, wherein the at least one calibration phantom includes a radiopaque step-wedge and a radiopaque rod.

* * * * *

UNITED STATES PATENT AND TRADEMARK OFFICE
Certificate

Patent No. 8,000,441 B2                          Patented: August 16, 2011

On petition requesting issuance of a certificate for correction of inventorship pursuant to 35 U.S.C. 256, it has been found that the above identified Patent, through error and without any deceptive intent, improperly sets forth the inventorship.

Accordingly, it is hereby certified that the correct inventorship of this Patent is: Philipp Lang, Lexington, MA (US); Siau-Way Liew, Pinole, CA (US); and Rene Vargas-Voracek, Sunnyvale, CA (US).

Signed and Sealed this Twenty-fourth Day of July 2012.

MINH-TOAN TON
*Supervisory Patent Examiner*
Art Unit 28
Technology Center 2800

UNITED STATES PATENT AND TRADEMARK OFFICE
Certificate

Patent No. 8,000,441 B2

Patented: August 16, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Philipp Lang, Lexington, MA (US); Siau-Way Liew, Pinole, CA (US); and Rene Vargas-Voracek, Sunnyvale, CA (US).

Signed and Sealed this Twenty-First Day of August 2012.

MINH-TOAN TON
*Supervisory Patent Examiner*
Art Unit 2882
Technology Center 2800